United States Patent
Bergmaier (10) Patent No.: US 8,361,778 B2
(45) Date of Patent: Jan. 29, 2013

(54) COMPOSITION COMPRISING ENZYMATICALLY DIGESTED YEAST CELLS AND METHOD OF PREPARING SAME

(75) Inventor: Dirk Bergmaier, Marklohe (DE)

(73) Assignee: Chr. Hansen A/S, Horsholm (DK)

( * ) Notice: Subject to any disclaimer, the term of this patent is extended or adjusted under 35 U.S.C. 154(b) by 1084 days.

(21) Appl. No.: 12/090,112

(22) PCT Filed: Oct. 16, 2006

(86) PCT No.: PCT/EP2006/067462
§ 371 (c)(1),
(2), (4) Date: Aug. 18, 2008

(87) PCT Pub. No.: WO2007/042577
PCT Pub. Date: Apr. 19, 2007

(65) Prior Publication Data
US 2009/0123990 A1    May 14, 2009

(30) Foreign Application Priority Data

Oct. 14, 2005   (EP) .................................. 05389001

(51) Int. Cl.
*C12N 1/20* (2006.01)
*C12N 1/00* (2006.01)
(52) U.S. Cl. ............. 435/252.9; 435/254.1; 435/255.1
(58) Field of Classification Search ............. 435/252.9, 435/254.1, 255.1
See application file for complete search history.

(56) References Cited

U.S. PATENT DOCUMENTS

| | | | | |
|---|---|---|---|---|
| 4,032,663 A | * | 6/1977 | Kobayashi et al. | 426/51 |
| 5,288,509 A | * | 2/1994 | Potman et al. | 426/60 |
| 5,932,455 A | * | 8/1999 | Viljava et al. | 435/139 |
| 6,159,724 A | * | 12/2000 | Ehret | 435/252.1 |
| 6,294,166 B1 | | 9/2001 | Hsia | |
| 2004/0115779 A1 | * | 6/2004 | Olsen et al. | 435/105 |

FOREIGN PATENT DOCUMENTS

| | | |
|---|---|---|
| GB | 1 516 333 | 9/1974 |
| WO | WO 92/13068 | 8/1992 |
| WO | WO 2005/003327 A1 | 1/2005 |

OTHER PUBLICATIONS

De Man et al. (A Medium for the Cultivation of Lactobacilli. J. Appl. Bact. 23(1), 130-135).*
Briggs et al. (The Preservation of Lactobacilli by Freeze-drying. J. Gen. Microbiol. 12, 503-512).*
R. Dembczynski et al., "Growth characteristics and acidifying activity of *Lactobacillus rhamnosus* in alginate/starch liquid-core capsules", Enzyme and Microbial Technology 31 (2002) 111-115.

* cited by examiner

*Primary Examiner* — Karen Cochrane Carlson
*Assistant Examiner* — Natalie Moss
(74) *Attorney, Agent, or Firm* — Foley & Lardner LLP (57) ABSTRACT

The present invention relates to the field of fermentation media. More specifically, the invention provides a method for preparing a composition useful for culturing microbial cells wherein whole and/or autolysed yeast cells are enzymatically treated to obtain the composition. The microbial cultures obtained have increased stability and are useful in the manufacturing of food, feed and as a pharmaceutical product.

22 Claims, 6 Drawing Sheets

COMPOSITION COMPRISING ENZYMATICALLY DIGESTED YEAST CELLS AND METHOD OF PREPARING SAME

FIELD OF THE INVENTION

The present invention relates to the field of fermentation media. More specifically, the invention provides a method for preparing a composition useful for culturing of microbial cells wherein whole and/or lysed yeast cells are enzymatically treated to obtain the composition. The microbial cultures obtained have increased stability and are useful in the manufacturing of food, feed and as a pharmaceutical product.

TECHNICAL BACKGROUND OF THE INVENTION

Microbial cultures are used extensively in the food, feed and pharmaceutical industry in the manufacturing of fermented products including most dairy products such as cheese, yoghurt and butter, but also in meat, bakery, wine or vegetable products. Additionally, specific microbial cultures may be used as probiotic agents and formulated as tablets, capsules etc and provided to animals including humans for their general health improving effects. Thus, microbial cultures may be provided for several purposes they do, however, all need to be cultivated prior to any delivery.

The production of a microbial organism involves the inoculation of microbial cells in a specific fermentation medium with an appropriate number of the cells to be propagated under appropriate fermentation conditions. Obviously, a high concentration of microbial cells is desired at the end of the fermentation. Thus, the fermentation process i.e. the fermentation conditions and the fermentation medium, are sought optimised in order to have a cost effective production resulting in a high biomass yield.

Industrial fermentations are carried out using complex undefined fermentation media. Major components of such media can be yeast extract, cornstarch, whey protein or other milk based media, which all have complex compositions. For selected fermentations chemically defined media are used. Often, the composition of the fermentation medium may be optimal for the viability of the microbial cells, but not optimal for obtaining a high biomass yield of the microorganism.

There have been various conventional approaches to provide methods for the optimisation of the fermentation media for obtaining increased biomass yields including chemical analysis, removal and/or addition of single components, various fermentation types, optimisation of the fermentation conditions such as temperature and pH, mutant selection and genetic engineering of the microorganism.

SUMMARY OF THE INVENTION

During the experimental work leading to the present invention, it was surprisingly found that it is possible to enhance the biomass yield during aerobic or anaerobic cultivation or production of a microbial culture by an in situ enzymatic digestion of whole and/or autolysed yeast cells as an essential part of the industrial fermentation media. This new media results in an altered final product with new nutritional and functional characteristics. Accordingly, the present invention provides a completely novel approach to increasing microbial cell biomass yield during fermentation.

In addition, it was found that the enzymatic digestion (esp. with proteases) of the whole or autolysed yeast cells reduces the allergenicity of the digest; of the fermentation medium; and of the products obtainable by using said medium for fermentation. Thus, the allergenicity of the compositions of the invention is anticipated to be low.

In accordance with these surprising findings, the present invention relates to a method for preparing a culture of a viable microorganisms, said method comprises growing the microorganisms in a medium comprising whole yeast cells and/or a lysate (e.g. an autolysate) thereof, which has been treated with one or more enzymes that are capable of digesting cell components, including the cell wall components, proteins, carbohydrates, nucleic acids etc. The invention also relates to a culture obtainable by the method of the invention, which culture can be distinguished from other cultures by the content of e.g. enzymatically digested yeast cell wall components. The novel cultures seem to be more stable and viable and have a prolonged storage time.

Conventionally, yeast extracts are used in the formulation of culture growth medium. The extracts are produced by polishing (e.g. filtration) autolyzed yeast and then concentrating the soluble fraction. The resulting powder or paste may then be used in the formulation of media for the growth of bacterial cultures. The major difference between the present composition and traditionally used yeast extract is the presence of all nutrients, soluble and insoluble, that are an integral part of the yeast cells (e.g. solubles as amino acids, peptides, proteins, vitamins, trace minerals, cell wall components e.g. polysaccharides, mannans beta-glucans etc.). These nutrients are then tailored by enzymatic treatments, as described in the method for preparation of the composition of the invention. The soluble fraction of the whole and/or autolysed yeast cells, which are present in the composition of the invention, is subsequently utilised by the bacterial cells during the fermentation process. Furthermore, unused parts of the insoluble components, originating from the yeast, are present in the final product, i.e. a concentrated and stable biomass. These components may exert a protective effect on the bacterial cultures during the downstream processing and the storage of the final product.

DETAILED DISCLOSURE OF THE INVENTION

In a first embodiment, the present invention relates to a method for preparing a composition comprising a culture of a viable microorganisms, said method comprises the following steps:
a) providing an aqueous suspension of whole yeast cells and/or a lysate (e.g. an autolysate) thereof;
b) treating the yeast cells and/or the lysate thereof with one or more enzymes selected from the group consisting of: an enzyme capable of digesting cell components, an enzyme capable of digesting the yeast cell wall, a proteinase, a lipase, a glucanase, an amylase, a nuclease, and a lyase; and
c) optionally inactivating the activity of the enzyme(s);
d) optionally repeating step b) or steps b) and c);
e) inoculating said treated suspension with a microorganism (of a desired strain).

It should be understood that the term "composition" denotes an aqueous suspension of microorganisms, as well as the microorganisms as such, e.g. isolated from the growth medium, and optionally further processed e.g. by freeze-drying or granulation. U.S. Pat. No. 6,159,724 discloses a process for preparing a sour dough for direct use for panification, said method comprises mixing yeast autolysate with wheat germs (and optionally whole meal wheat) and subjecting the wheat starch and gluten to hydrolysis with alpha-amylase, amyloglucosidase, papaine and pancreatine. The resulting medium is inoculated with *Saccharomyces cerevisiae steineri* DSM9211 and one or more strains selected from the group consisting of: *Lactobacillus brevis* DSM9209, *Lactobacillus plantarum* DSM9208, *Leuconostoc mesenteroides* DSM9207 and *Pediococcus pentosaceus* DSM9210. This disclosure differs from the present invention in that:

The lactic acid bacteria is selected from four specific strains;

The sour dough contains a specific yeast strain, ie is a mixed culture of a living yeast strain and at least one bacterial strain;

The viscosity of the sour dough preparation is high; and not usable for use a starter culture for eg fermented milk.

Wheat germs and/or whole meal is used in an amount exceeding seven times the amount of yeast autolysate;

four specific enzymes are used, ie amyloglucosidase, alpha-amylase, papaine and pancreatine; etc.

Thus, the method of the present invention should preferable comprise one or more of the following features:

the suspension in step a) does not contain wheat germs and/or whole meal in an amount exceeding 5 times (such as not exceeding 3 times, 2 times, 1 time, 0.5 times, 0.3 times, 0.1 times) the total amount of yeast cells and the lysate thereof, and it is presently preferred that the suspension in a) is substantially free (most preferred free) of wheat germs and/or whole meal;

the propagated microorganisms are separated from the culture medium/harvested;

the produced microorganisms are not a mixed yeast/bacterial culture, it is presently preferred that a monoculture is produced;

the microorganisms used for inoculation are not the same strains and/or species as in U.S. Pat. No. 6,159,724;

the enzymes used are not the same mixture as disclosed in U.S. Pat. No. 6,159,724.

It is emphasised in U.S. Pat. No. 6,159,724 that the enzymes are added in order to hydrolyse the wheat starch and gluten, ia for avoiding gelatinisation of the starch (see "Summary of the Invention" and claim 1), and not the yeast autolysate. Consequently, enzymes should not be added to a preparation without wheat germs. GB patent 1516333 discloses culture media for *Streptococcus lactis* and *S. cremoris* comprising autolyzed yeast, and U.S. Pat. No. 6,294,166 discloses a dry mixture of *Lactobacillus acidophilus* and powder yeast. No enzymes are added to these compositions and consequently they do not contain e.g. enzymatically digested yeast cell wall material.

The method of the invention may comprise a treatment of the aqueous suspension in step a) (eg in order to erupt or kill any viable yeast cells) by:

i) heating the suspension to a temperature in the range 40-100 degrees C. (eg in the range 60-80, 60-90 or 70-90 degrees), such as for a period of 2-30 min; and/or     ii) treating the yeast cells with a cell wall digesting enzyme, such as carried out at a pH in the range 5-8; at a temperature in the range 20-80 degrees C.; and/or for a period of 10 minutes to 24 hours; and/or     iii) erupting the yeast cells by chemical or mechanical means, such as by sonication, homogenisation and/or pressure treatment.

The method of the invention may further comprise steps that are known to the skilled person, such as one or more of the following steps:

aerating the mixture obtained in step e);

agitating the mixture obtained in step e);

isolating/harvesting the obtained microorganisms, such as by filtration or centrifugation;

drying the isolated microorganisms;

Freeze-drying the isolated microorganisms;

pelletizing the isolated microorganisms, preferably in (freeze) dried form;

packaging the isolated microorganisms.

In an embodiment the method for preparing a (composition comprising a) microbial culture in increased yields as described herein further comprises:

i) freezing said harvested/isolated microorganism to obtain frozen microbial cells.

Said method may further comprise:

ii) sublimating water from said frozen cells to obtain freeze-dried cells.

Said in another way, wherein the harvested microorganism culture is converted into a freeze-dried cell culture.

The method may further comprise:

iii) packing said cells obtained in step i) or ii).

Preferably at least one cryoprotectant is added to the harvested microorganism. Preferably, the cryoprotective agent(s) is selected from the group consisting of one or more compound(s) involved in the biosynthesis of nucleic acids or one or more derivative(s) of any such compounds. Examples of preferred cryoprotective agent(s) is described in an earlier filed patent application with application number PCT/DK2004/000477. Preferred cryoprotective agent(s) described in PCT/DK2004/000477 are also preferred cryoprotective agent(s) of the present invention. The complete description of PCT/DK2004/000477 is incorporated by reference herein.

Also, the method may comprise adding a (i.e. one or more) nutrient component(s) known to the skilled person, such as components selected from the group consisting of: a carbohydrate, a yeast extract, a beef extract, a peptone (e.g. a soy peptone, a wheat peptone, or a whey peptone), a vitamin, a peptide, a protein, a mineral salt, a growth factor and a lipid; preferably before or/and after step e).

The enzyme(s) in step b) is preferably heterologous to the yeast cell to be treated, such as an enzyme originating from a different yeast species, of non-yeast origin, of bacterial origin (such as originating from a *Bacillus* species, e.g. *B. subtilis*) or of fungal origin (such as originating from an *Aspergillus* species), but also enzymes native to the yeast cells may be added.

Examples on the enzyme that might be used in step b) are a protease selected from the group consisting of: an enzyme belonging to the class EC 3.4.-.-, especially class 3.4.21.62, Protease N (Amano), subtilisin, and Alcalase (Novozymes);

a lysing enzyme selected from the group consisting of: an enzyme belonging to the class EC 3.4.24.-, bacillolysin, YL-NL (Amano);

a nuclease selected from the group consisting of: an enzyme belonging to the class EC 3.1.3.- or 3.1.4.- (especially EC 3.1.4.1), a Rnase, a DNase, an exonuclease;

an amylase selected from the group consisting of: an enzyme belonging to class EC 3.2.1.-, alpha amylase, amyloglucosidase;

a lipase selected from the group consisting of: an enzyme belonging to class EC 3.1.1.-;

a mixture of any of the above enzymes.

Step b) may be carried out at a temperature in the range 25 to 90 degrees C., such as in the range 35-80 degrees C. or in the range 50-70 degrees C., and step c) may comprise heating to a temperature in the range 60-130 degrees C., such as autoclaving, sterilizing (e.g. UHT) or pasteurizing.

The yeast source may be digested with one or more suitable enzyme(s) for a period of time, and under conditions, resulting in a high activity of the enzyme. When e.g. a protease is used it is suitable to obtain an AN/TN ratio in the range of 5-60% such as in the range of 10-50% such as 25-45%, such as 5-20%. It follows that a suitable result will depend on the yeast source, type of enzyme(s), amount of enzyme etc.

Typically, the amount of enzyme used is in the range of 5-80 U/g yeast, such as 10-50 U/g yeast when a lysing enzyme such as the Amano YL-NL is used, in the range of 100-10.000 U/g yeast such as in the range of 700-5000 U/g yeast, such as 1000-8000 U/g yeast when a protease such as Protease N is used, in the range of 0.01 to 1%, such as 0.03 to 0.2% (w/w of the total culture media) when a protease such as Alcalase is used.

It is anticipated that all types of yeast cells may be used in the invention. Examples of the yeast cells in step a) are yeasts selected from the group consisting of: a *Torula* species, baker's yeast, brewer's yeast, a *Saccharomyces* species such as *S. cerevisiae*, a *Schizosaccharomyces* species, a *Pichia* species such as *Pichia pastoris*, a *Candida* species, a *Hansenula* species such as *Hansenula polymorpha*, and a *Klyuveromyces* species such as *Klyuveromyces lactis*. Also mixture of any of these species might be used.

It is anticipated that the enzymatic treatment of the yeast cells may be performed most conveniently before the inoculation in step e), e.g. that the enzyme is added to the suspension of the yeast and/or the lysate thereof, or the yeast cells and/or the lysate thereof are added to an aqueous suspension of the enzyme, but the treatment may also be performed during the growth of the microorganisms, depending on the kind of enzymatic treatment.

However, esp. when the enzymes present in the yeast cells will interfere with any further enzymatic treatment, step a) may be succeeded by an enzyme inactivating step, such as a step as defined for step c).

It is anticipated that the digested yeast cells will provide a medium (or medium supplement) for all microorganisms (esp. Gram positive bacteria, Gram negative bacteria, yeasts and fungi). A suitable microorganism is selected from the group consisting of: a lactic acid bacteria; a *Lactobacillus* species, such as *Lactobacillus acidophilus, Lactobacillus casei, Lactobacillus bulgaricus, Lactobacillus helveticus*; and a *Lactococcus* species, such as *Lactococcus lactis, Lactococcus cremoris, Lactococcus diacetylactis* and *Lactococcus thermophilus*; and a *Leuconostoc* species, such as *Leuconostoc cremoris*. The culture may comprise one or more organisms selected from the group comprising *Bifidobacterium* spp., *Brevibacterium* spp., *Propionibacterium* spp., *Lactococcus* spp. including *Lactococcus lactis* subsp. *lactis* and *Lactococcus lactis* subsp. *cremoris, Lactobacillus* spp. including *Lactobacillus acidophilus, Streptococcus* spp., *Enterococcus* spp., *Pediococcus* spp., *Leuconostoc* spp., *Oenococcus* spp. and fungal spp. including *Penicillium* spp., *Cryptococcus* spp., *Debaryomyces* spp., *Klyveromyces* spp. and *Saccharomyces* spp. The culture may comprise one or more mesophilic organisms as described herein and/or one or more thermophilic organisms as described herein. The culture may be an O-culture that comprises one or more organisms selected from the group comprising *Lactococcus lactis* subsp. *lactis* and *Lactococcus lactis* subsp. *cremoris*. The culture may be a LD-culture that comprises one or more organisms selected from the group comprising *Lactococcus lactis* subsp. *lactis, Lactococcus lactis* subsp. *cremoris, Lactococcus lactis* subsp. *lactis* biovar. diacetylactis and *Leuconostoc mesenteroides* subsp. *cremoris*. It is presently preferred that the culture is a LAB-culture that comprises one or more organisms selected from the group consisting of *Lactococcus* spp., *Streptococcus* spp., *Enterococcus* spp., *Lactobacillus* spp. such as *Lactobacillus acidophilus* or *L. plantarum*, *Leuconostoc* spp., *Pediococcus* spp. and *Bifidobacterium* spp.

The obtained composition comprises a high ratio of viable microorganisms, thus, it is contemplated that the method of the invention is very suitable for preparing a starter culture or a probiotic culture. In accordance herewith, the invention also relates to a composition comprising a viable microorganism (e.g. a starter culture or a probiotic composition) obtainable by the method of the invention, and a composition comprising viable bacteria cells (e.g. lactic acid bacteria as defined above) and cell wall components originating from yeast, e.g. from lysed yeast cells (such as autolysed yeast cells) and/or yeast cells treated with a cell wall digesting enzyme.

The composition of the invention may be:
in the form of a powder, a pellet or an aqueous suspension, and/or
in a frozen or freeze-dried form; and/or
packaged.

The composition of the invention is usable as a pharmaceutical or a food additive, either in a form as defined above or formulated in a form known to the skilled person.

In an embodiment, especially when the microorganism is a lactic acid bacteria, the composition of the invention may be used to produce a fermented product such as a dairy product, ensilage, pickled vegetables etc. The invention also relates to such a product, especially a fermented milk product, which is obtainable by a method which comprises inoculating milk with a composition of the invention.

In a further embodiment, the invention relates to a composition which is obtainable by:
a) providing an aqueous suspension of whole yeast cells belonging to a *Torula* species and/or a lysate (such as an autolysate) thereof;
b) treating the yeast cells and/or the lysate thereof with one or more enzymes as previously defined for step b); and
c) optionally inactivating the activity of the enzyme(s);
d) optionally repeating step b) or steps b) and c); and
e) optionally drying (such as freeze-drying).

Such a composition is useable as an additive for growth of microorganisms, such as in the method of the present invention. More specifically, this composition of the present invention is useful as a growth medium for the production of microbial cells. The culturing of cells in the composition of the invention may result in enhanced bacterial growth, a higher yield of biomass, and an increased stability of the final product i.e. the microbial culture. An essential component of the present composition is whole and/or autolyzed yeast that is digested in situ with specific enzymes. The resulting broth will be addressed herein as "yeast digest". This yeast digest is suitable as a component in a growth media for culturing of microbial cells.

In a still further embodiment, the invention relates to a method for preparing a culture of lactic acid bacteria, which comprises the following steps:
a) providing an aqueous suspension of whole yeast cells and/or lysed (e.g. autolysed) yeast cells;
b) treating the yeast cells and/or the lysate thereof with an enzyme as previously defined for step b);
c) optionally inactivating the enzymatic activity;
d) optionally repeating the step b) or step b) and c);
e) inoculate with a lactic acid bacteria; and
f) optionally adding a (i.e. one or more) nutrient component(s) selected from the group consisting of: a carbohydrate, a yeast extract, a beef extract, a peptone (e.g. a soy peptone, a wheat peptone, or a whey peptone), a vitamin, a peptide, a protein, a mineral salt, a growth factor and a lipid; preferably before or/and after step e).

In a preferred embodiment of the methods according to the invention, the culturing of the microorganism is done performed under industrial conditions. Accordingly, a preferred embodiment is wherein the OD of the culture medium reached a OD of from $OD_{600}=10$ to $OD_{600}=200$, more preferably a OD of from $OD_{600}=15$ to $OD_{600}=100$ and most preferably a OD of from $OD_{600}=20$ to $OD_{600}=80$.

Further, a preferred embodiment is wherein the culturing is performed in a large scale fermentor comprising of from 5 L to 100.000 L culture medium, preferably of from 300 L to 20.000 L culture medium. A preferred embodiment is wherein the culturing comprises control of temperature and/or pH. The microorganism may be cultured under anaerobic conditions or under aerobic conditions.

Having generally described the embodiments of the present composition and methods, the invention will now be described using specific Examples and figures. The Examples and figures further illustrate various features and advantages of the invention, but are not intended to limit the scope of the invention.

Definitions

In the present context any enzyme capable of breaking down components of the whole yeast or the autolysed yeast may be used. Enzymes of particular interest are nucleases such as e.g. 5'-ribonucleases capable of degrading RNA to nucleotides.

As used herein, the term "fermentation" refers to a process of propagating or cultivating a microbial cell under both aerobic and anaerobic conditions.

The term "starter culture" refers to a preparation containing microbial cells that is intended for inoculating a medium to be fermented.

In the present context, the term "microorganism" is used in its normal meaning. Thus, in its broadest meaning the term "microorganism" is intended to cover algae, protozoa, viruses, bacteria and fungi. Preferred microorganisms are bacteria and fungi, in particular bacteria, such as lactic acid bacteria.

In the present context, the expression "lactic acid bacteria" designates a group of Gram positive, catalase negative, non-motile, microaerophilic or anaerobic bacteria which ferment sugar with the production of acids including lactic acid as the predominantly produced acid, acetic acid, formic acid and propionic acid. The industrially most useful lactic acid bacteria are found among *Lactococcus* species, *Streptococcus* species, *Enterococcus* species, *Lactobacillus* species, *Leuconostoc* species, *Pediococcus* species and *Bifidobacterium* species.

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include Lactococcus lactis, *Lactococcus lactis* subsp. *cremoris*, *Leuconostoc mesenteroides* subsp. *cremoris*, *Pediococcus pentosaceus*, *Lactococcus lactis* subsp. *lactis* biovar. diacetylactis, *Lactobacillus casei* subsp. *casei* and *Lactobacillus paracasei* subsp. *paracasei*. Thermophilic lactic acid bacterial species include as examples *Streptococcus thermophilus*, *Enterococcus faecium*, *Lactobacillus delbrueckii* subsp. *lactis*, *Lactobacillus helveticus*, *Lactobacillus delbrueckii* subsp. *bulgaricus* and *Lactobacillus acidophilus*.

Also the strict anaerobic bacteria belonging to the genus *Bifidobacterium* including *Bifidobacterium bifidum* and *Bifidobacterium longum* are commonly used as dairy starter cultures and are generally included in the group of lactic acid bacteria. Additionally, species of *Propionibacterium* are used as dairy starter cultures, in particular in the manufacture of cheese. Additionally, organisms belonging to the *Brevibacterium* genus are commonly used as food starter cultures.

Another group of microbial starter cultures are fungal cultures, including yeast cultures and cultures of filamentous fungi, which are particularly used in the manufacture of certain types of cheese and beverage. Examples of fungi include *Penicillium roqueforti*, *Penicillium candidum*, *Geotrichum candidum*, *Torula kefir*, *Saccharomyces kefir* and *Saccharomyces cerevisiae*.

A significant application of the starter culture according to the invention is as so-called probiotics or probiotic agents. In the present context, the term "probiotic" and "probiotic agent" is used interchangeably and is to be understood as microbial cultures which, when ingested in the form of viable cells by humans or animals, confer an improved health condition e.g. by suppressing harmful microorganisms in the gastrointestinal tract, by enhancing the immune system or by contributing to the digestion of nutrients. A typical example of such a probiotically active product is "sweet acidophilus milk".

The term "substantially free" from a particular substance preferably refers to a condition in which the substance is present in a minor or trace amount, more preferably less than about 5% weight per weight.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

(AN) content. The AN/TN ratio was calculated using a TN value that was determined previously for the 10% solution for each yeast source, assuming that the TN value does not change during digestion.

EXAMPLES

Example 1

Enzymatic Digestion of Yeast Sources

Suspensions of two different yeast sources (see Table 1) were prepared in water at a 10% (w/w) concentration for a final volume of 300 ml. The suspensions were heated to 90° C. for 20 min, then cooled to about 50° C. The pH was adjusted to the values indicated in Table 3 before dividing into 12 ml portions. Different enzymes (see table 2) were then added to the suspensions. Each yeast suspension was treated with the lysing enzyme Amano YL-NL and the proteolytic enzymes Protease N (Amano) and Alcalase at the enzyme concentrations, times, pH and temperatures indicated in table 3. In some cases a second enzyme digestion step was carried-out as indicated in table 3. After digestion, the samples were rapidly cooled on ice until analyzed for their amino-nitrogen

TABLE 1

Yeast sources

| Product name | Type of yeast | Manufacturer |
|---|---|---|
| Aventine 62-P | Brewers' whole yeast | Aventine Renewable Energy |
| Provesta 027 | Torula yeast autolysate | Provesta Flavor Ingredients |

TABLE 2

Enzymes

| Enzyme | Manufacturer | Function |
|---|---|---|
| YL-NL "Amano" | Amano Enzyme Inc. | Lysis of yeast cells |
| Protease N | Amano Enzyme Inc. | Protein hydrolysis |
| Alcalase | Novozymes | Protein hydrolysis |

TABLE 3

Enzymatic digestion of different yeast sources with proteolytic and lytic enzymes.

| # | Yeast source | Enzyme 1 | Concentration (U/g yeast) | Enzyme 2 | Concentration (U/g yeast) | Time (hrs) | pH | Temp |
|---|---|---|---|---|---|---|---|---|
| 1 | Aventine | | No enzymes | | | 0 | 6.5 | 50 |
| 2 | Aventine | | No enzymes | | | 16 | 6.5 | 50 |
| 3 | Aventine | YL-NL | 21 | Prot N | 700 | 1 | 6.5 | 50 |
| 4 | Aventine | YL-NL | 21 | Prot N | 2000 | 1 | 6.5 | 50 |
| 5 | Aventine | YL-NL | 21 | Prot N | 5000 | 1 | 6.5 | 50 |
| 6 | Aventine | YL-NL | 21 | Prot N | 700 | 2 | * | 50 |
| 7 | Aventine | YL-NL | 21 | Prot N | 2000 | 2 | * | 50 |
| 8 | Aventine | YL-NL | 21 | Prot N | 5000 | 2 | * | 50 |
| 9 | Aventine | YL-NL | 7 | | | 1 | 6 | 50 |
| 10 | Aventine | YL-NL | 21 | | | 1 | 6 | 50 |
| 12 | Aventine | YL-NL | 35 | | | 1 | 6 | 50 |
| 11 | Aventine | YL-NL | 21 | | | 16 | 6 | 50 |
| 13 | Aventine | Prot N | 700 | | | 1 | 7.5 | 50 |
| 14 | Aventine | Prot N | 2000 | | | 1 | 7.5 | 50 |
| 16 | Aventine | Prot N | 5000 | | | 1 | 7.5 | 50 |
| 15 | Aventine | Prot N | 2000 | | | 16 | 7.5 | 50 |
| 17 | Aventine | YL-NL | 21 | Alcalase | 0.0072 | 2 | ** | ** |
| 18 | Aventine | YL-NL | 21 | Alcalase | 0.024 | 2 | ** | ** |
| 19 | Aventine | YL-NL | 21 | Alcalase | 0.048 | 2 | ** | ** |
| 20 | Aventine | Alcalase | 0.0003 | | | 1 | 7 | 60 |
| 21 | Aventine | Alcalase | 0.001 | | | 1 | 7 | 60 |
| 23 | Aventine | Alcalase | 0.002 | | | 1 | 7 | 60 |
| 22 | Aventine | Alcalase | 0.001 | | | 16 | 7 | 60 |
| 24 | Provesta | | No enzymes | | | 0 | 7 | 50 |
| 25 | Provesta | | No enzymes | | | 16 | 7 | 50 |
| 26 | Provesta | YL-NL | 21 | | | 1 | 6 | 50 |
| 27 | Provesta | YL-NL | 21 | Prot N | 2000 | 1 | 6.5 | 50 |
| 28 | Provesta | Prot N | 700 | | | 1 | 7.5 | 50 |
| 29 | Provesta | Prot N | 2000 | | | 1 | 7.5 | 50 |
| 31 | Provesta | Prot N | 5000 | | | 1 | 7.5 | 50 |
| 30 | Provesta | Prot N | 2000 | | | 16 | 7.5 | 50 |
| 32 | Provesta | Alcalase | 0.0072 | | | 1 | 7 | 60 |
| 33 | Provesta | Alcalase | 0.024 | | | 1 | 7 | 60 |
| 35 | Provesta | Alcalase | 0.048 | | | 1 | 7 | 60 |
| 34 | Provesta | Alcalase | 0.024 | | | 16 | 7 | 60 |

| # | Rep 1 AN/TN | Rep 2 AN/TN | Rep 3 AN/TN | Rep 4 AN/TN | Mean AN/TN | ST DEV AN/TN | Std Err | Ranking |
|---|---|---|---|---|---|---|---|---|
| 1 | 5.709 | 5.802 | 6.031 | 5.637 | 5.795 | 0.171 | 0.086 | S |
| 2 | 5.728 | 5.877 | 6.068 | 6.390 | 6.016 | 0.286 | 0.143 | S |
| 3 | 7.025 | 7.976 | 9.473 | 10.867 | 8.835 | 1.688 | 0.844 | Q R |
| 4 | 11.586 | 10.807 | 11.524 | 10.579 | 11.124 | 0.507 | 0.254 | L M N O |
| 5 | 13.275 | 13.720 | 12.220 | 11.760 | 12.744 | 0.909 | 0.454 | J K L |

TABLE 3-continued

Enzymatic digestion of different yeast sources with proteolytic and lytic enzymes.

| 6 | 10.673 | 11.731 | 11.620 | 12.453 | 11.619 | 0.731 | 0.366 | K L M N O |
|---|---|---|---|---|---|---|---|---|
| 7 | 11.678 | 12.533 | 14.759 | 13.803 | 13.193 | 1.361 | 0.680 | I J K |
| 8 | 14.590 | 14.271 | 14.475 | 16.735 | 15.018 | 1.152 | 0.576 | F G H |
| 9 | 8.829 | 7.964 | 8.125 | 8.647 | 8.391 | 0.413 | 0.206 | R |
| 10 | 11.137 | 13.307 | 9.766 | 9.455 | 10.916 | 1.754 | 0.877 | M N O |
| 12 | 14.490 | 12.980 | 11.373 | 9.859 | 12.176 | 2.001 | 1.001 | J K L M N |
| 11 | 11.731 | 12.798 | 12.527 | 13.618 | 12.668 | 0.778 | 0.389 | J K L |
| 13 | 10.522 | 10.694 | 11.199 | 9.528 | 10.486 | 0.700 | 0.350 | N O P Q |
| 14 | 10.780 | 10.737 | 9.000 | 9.364 | 9.970 | 0.922 | 0.461 | O P Q R |
| 16 | 14.634 | 15.186 | 12.595 | 11.819 | 13.559 | 1.608 | 0.804 | H I J |
| 15 | 14.046 | 15.011 | 15.193 | 14.834 | 14.771 | 0.505 | 0.253 | F G H I |
| 17 | 12.908 | 11.742 | 11.417 | 11.801 | 11.967 | 0.650 | 0.325 | J K L M N |
| 18 | 12.772 | 14.072 | 12.478 | 11.097 | 12.605 | 1.221 | 0.610 | J K L M |
| 19 | 12.928 | 12.589 | 11.873 | 10.466 | 11.964 | 1.091 | 0.546 | J K L M N |
| 20 | 9.005 | 7.864 | 9.849 | 9.722 | 9.110 | 0.910 | 0.455 | P Q R |
| 21 | 11.289 | 9.665 | 9.679 | 9.693 | 10.081 | 0.805 | 0.403 | O P Q R |
| 23 | 11.615 | 11.667 | 10.052 | 12.558 | 11.473 | 1.042 | 0.521 | L M N O |
| 22 | 11.569 | 10.705 | 11.632 | 9.289 | 10.799 | 1.092 | 0.546 | N O P |
| 24 | 12.564 | 13.007 | 17.658 | 14.641 | 14.467 | 2.307 | 1.154 | G H I |
| 25 | 15.161 | 16.013 | 15.591 | 14.703 | 15.367 | 0.563 | 0.282 | E F G |
| 26 | 16.921 | 17.534 | 15.376 | 15.442 | 16.318 | 1.080 | 0.540 | B C D E F |
| 27 | 17.567 | 17.602 | 19.254 | 16.225 | 17.662 | 1.240 | 0.620 | A B |
| 28 | 15.718 | 15.296 | 16.449 | 15.910 | 15.843 | 0.478 | 0.239 | C D E F G |
| 29 | 17.243 | 17.865 | 15.631 | 17.575 | 17.079 | 0.998 | 0.499 | B C D |
| 31 | 18.007 | 16.913 | 16.304 | 16.457 | 16.920 | 0.769 | 0.385 | B C D E |
| 30 | 18.366 | 19.628 | 18.895 | 19.235 | 19.031 | 0.535 | 0.268 | A |
| 32 | 16.457 | 10.116 | 8.861 | 12.342 | 11.944 | 3.335 | 1.668 | J K L M N |
| 33 | 16.654 | 14.228 | 14.621 | 16.729 | 15.558 | 1.319 | 0.660 | D E F G |
| 35 | 16.514 | 18.070 | 17.896 | 17.107 | 17.397 | 0.723 | 0.361 | A B C |
| 34 | 17.139 | 17.549 | 18.520 | 18.375 | 17.896 | 0.661 | 0.331 | A B |

Independent parameters are type of yeast source, type of enzymes, enzyme concentrations, total time of digestion, pH and temperature during digestion and price of the medium formulation. Dependent parameter is the measured AN/TN ratio. Results for AN/TN ratio are ranked with A being the highest value. Results with the same letter are not significantly (p = 0.05) different.

Example 2

Growth of *Lactobacillus acidophilus* La-5 on a Yeast Digest Based Medium

Materials & Methods

Microorganisms and Inoculum Preparation

*Lactobacillus acidophilus* La-5 (commercially available) was obtained from the Chr. Hansen Culture Collection (CHCC3777). The inoculum was prepared in MRS medium. Two 10-hour serial transfers, maintained anaerobically with the GasPak Plus system at 37° C. using a transfer volume of 0.7% (v/v) were conducted. The fermenters were inoculated with 0.7% (v/v) of the final culture.

Culture Media

An 10% (w/w) aqueous suspension of the yeast source (Aventine 62-P or Provesta 027) was prepared. The suspension was heated to 90° C. for 20 min. After that period, the temperature and pH value were adjusted and controlled, the specific enzyme(s) were added and the digestion was carried-out. Optionally, the digestion was completed by the addition of a second enzyme followed by a second digestion period. The resulting suspension is referred to as "yeast digest".

The medium was prepared by adding several other components (e.g. water, carbohydrates, mineral salts, and commercial yeast extracts if needed) to make it a complete medium for optimal growth of the micro-organisms. A partial composition of the medium is indicated in table 4. The medium was sterilized at 121° C. for 20 min and then cooled down rapidly on ice.

TABLE 4

Composition of the yeast digest based medium.

| Component | Amount (% w/w) |
|---|---|
| Yeast source | 1.75 |
| Proteolytic enzyme (e.g. Alcalase) | 0.08 |
| Yeast extract Biospringer 232 | 0.25, 0.55, 1 |
| Yeast extract Flavormate 957 | 0.25, 0.55, 1 |
| Sugar (e.g. dextrose monohydrate) | 4 |

Fermentations

Fermentations were carried-out in yeast digest based medium at 38° C. and pH regulated at a value of 5.5 by addition of 13.5N $NH_4OH$. The fermentations were performed in 2 L bioreactor (Xplora; Adaptive Biosystems, UK) with a working volume of 1.7 L. Initial pH of the culture medium was adjusted to 6.4 if necessary and the headspace was flushed with nitrogen before inoculation. Samples were taken at different time intervals, depending on base addition rate for analysis of residual sugar, L-lactic acid, and viable biomass concentration.

Cell Enumeration

Viable cell counts (CFU per millilitre) were determined by plating diluted samples on solid acidified MRS agar. Plates were incubated anaerobically using the GasPak Plus system (BBL) at 37° C. for two days.

Results

A) Effect of the Concentration of Additional Yeast Extract on Growth.

As indicated in table 4, three levels of addition of the two yeast extracts Biospringer 232 (Bio Springer, Maisons-Alfort, France) and Flavormate 957 (Sensient Bionutrients, Indianapolis, Ind., USA) were tested, 0.25, 0.55 and 1% of each yeast extract. All other parameters except for the type of yeast used for the yeast digest were kept constant.

Figure 1:
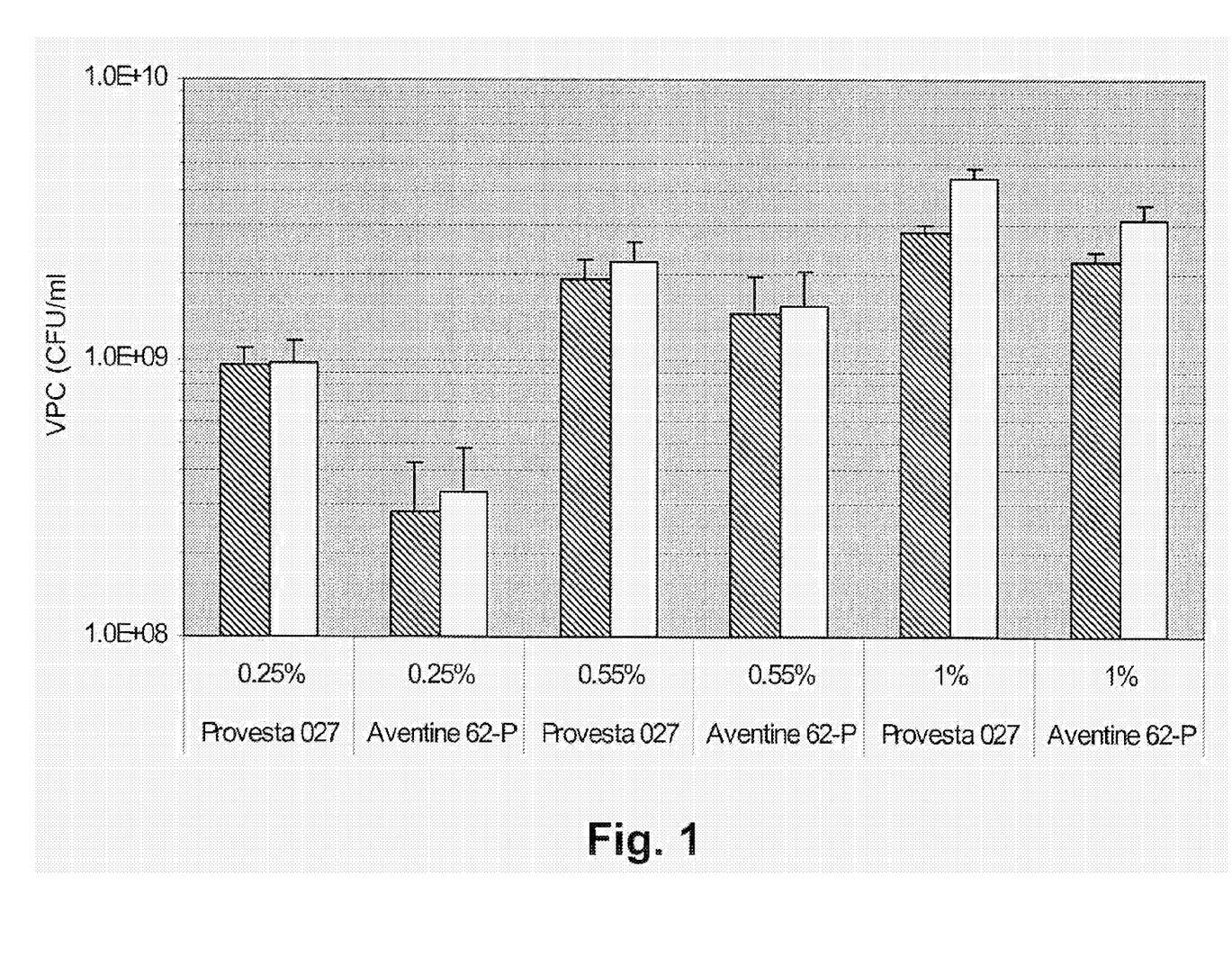
FIG. 1: Cell counts of *L. acidophilus* La-5 at the time of glucose depletion (dashed bars) and at the end of fermentation (plain bars). Yeast digest based media at additional yeast extract additions of 0.25, 0.55 and 1%.

FIG. 1 shows the data for final cell counts at the time of glucose depletion and at the end of the fermentation (EOF). Data indicates that the total cell counts were low for a level of 0.25% of each yeast extract and that highest cell numbers were obtained at 1% addition of each yeast extract. The highest value of $4.4 \cdot 10^9$ CFU/ml was obtained for a Provesta 027 based yeast digest with 1% additional yeast extracts of Biospringer 232 and Flavormate 957.

B) Effect of the Type of Enzyme and the Procedure of Digestion (Time) on Growth

The level of yeast extract addition was kept at 0.25% but different digestion strategies, times and enzymes were applied.

Figure 2:
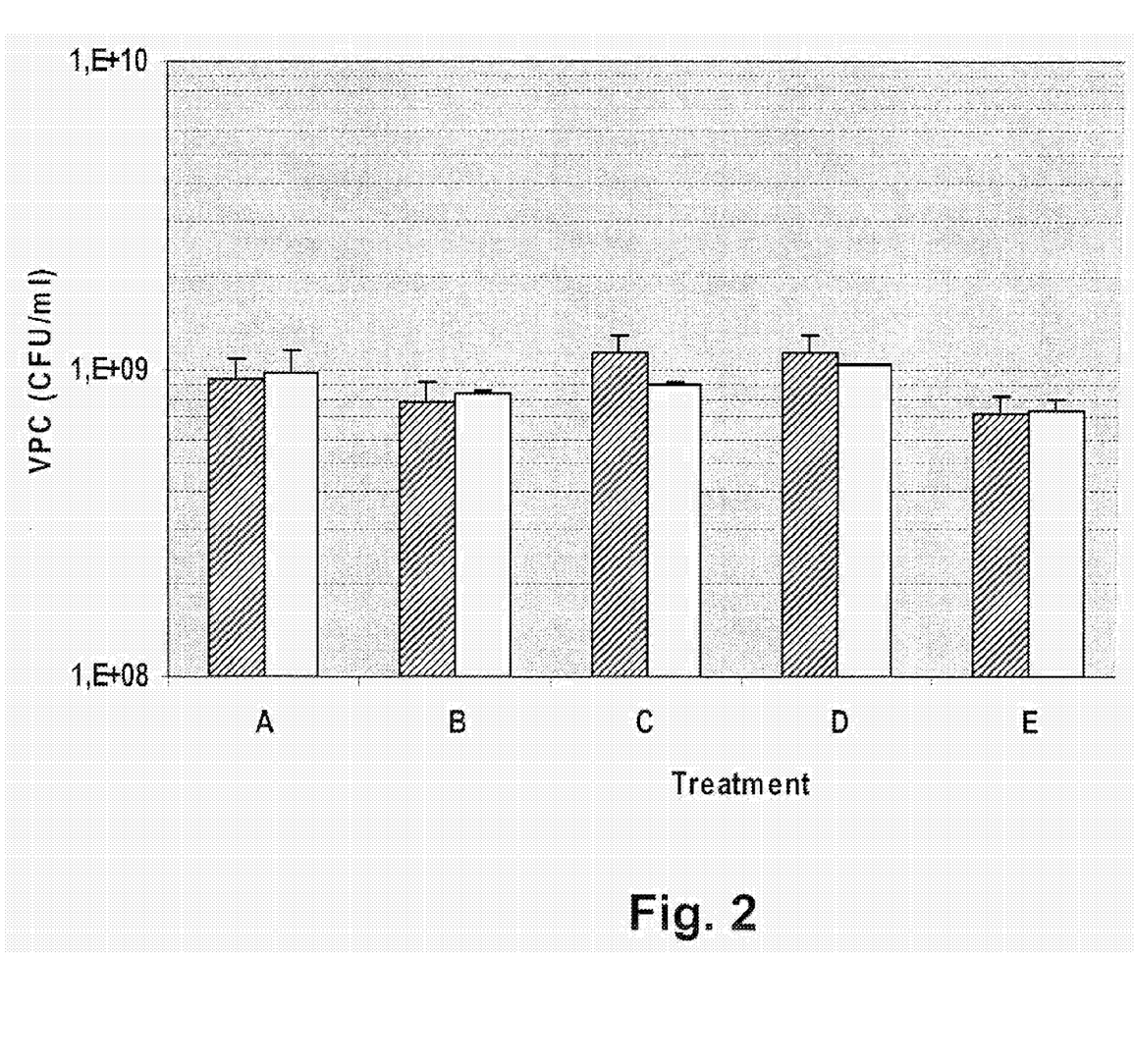
FIG. 2: Viable cell counts at time of glucose depletion (dashed bars) and at the end of fermentation (EOF) (plain bars) for *L. acidophilus* La-5 grown in digested Provesta 027. Influence of the type of enzyme and digestion strategy.

In a first set of experiments, Provesta 027 was used as yeast source. The different treatments are indicated in Table 5. For example, in treatment A, Provesta 027 was digested with Protease N at an enzyme concentration of 700 U/g yeast for 1 h. In treatment E, the β-glucanase Laminex (Genencor International Inc.; Rochester, N.Y., USA) was used at a concentration of 300 U/g yeast in a first step. In a second step, the proteotytic enzyme Alcalase was used. FIG. 2 shows the cell counts at the time of glucose depletion and at the end of the fermentation (EOF). The results show, that all enzymatic treatments tested in this study resulted in a digested Provesta 027 based medium that supports the growth of La-5.

TABLE 5

Different enzymatic treatments of Provesta 027.
Type of enzymes and digestion conditions.

| | | Enzyme 1 | | | | | Enzyme 2 | | | |
|---|---|---|---|---|---|---|---|---|---|---|
| Treatment | Type | Conc. (U/g) | T (° C.) | pH | t (h) | Type | Conc. (U/g) | T (° C.) | pH | t (h) |
| A | Prot N | 700 | 50 | 7.5 | 1 | — | — | — | — | — |
| B | Prot N | 2000 | 50 | 7.5 | 1 | — | — | — | — | — |
| C | Prot N | 1000 | 50 | 7.5 | 1 | YL-NL | 7 | 50 | 6.5 | 1 |
| D | Alcalase | 0.11 | 60 | 7 | 1 | — | — | — | — | — |
| E | Laminex | 300 | 60 | 5.2 | 1 | Alcalase | 0.11 | 60 | 7 | 1 |

Figure 3:
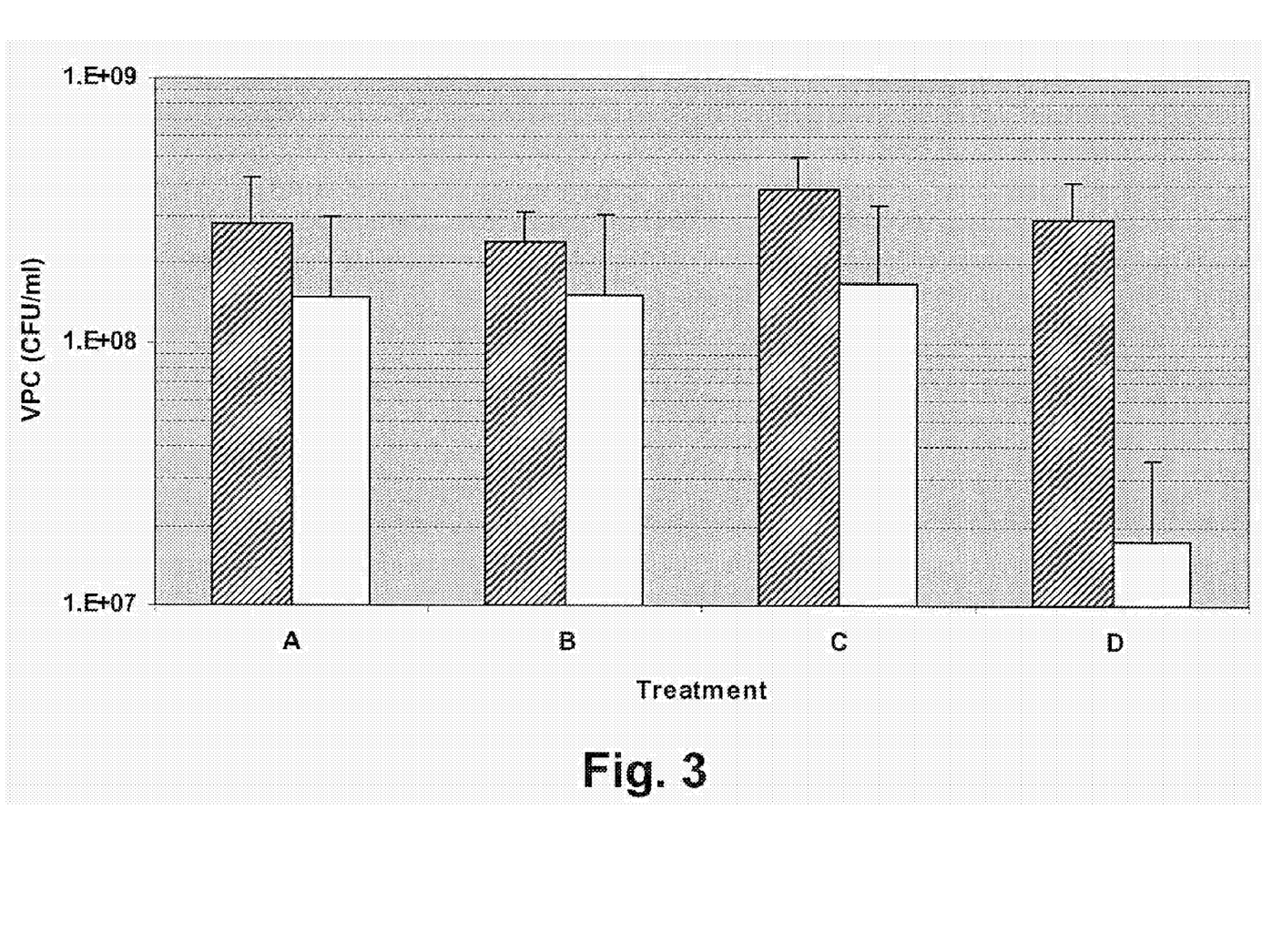
FIG. 3: Viable cell counts at time of glucose depletion (dashed bars) and at the end of fermentation (EOF) (plain bars) for *L. acidophilus* La-5 grown in digested Aventine 62-P. Influence of the type of enzyme and digestion strategy.

Similar experiments were conducted using the whole yeast Aventine 62-P. Four enzymatic treatments of this yeast source were conducted. Parameters of the digestion step are given in table 6. FIG. 3 shows the cell counts at the time of glucose depletion and at the end of the fermentation (EOF). In general, the cell counts for Aventine 62-P are lower than those for Provesta 027. The type of enzymatic treatment did not have any significant effect on the viable cell counts of La-5 in the digested Aventine 62-P based media.

TABLE 6

Different enzymatic treatments of Aventine 62-P.
Type of enzymes and digestion conditions.

| | | Enzyme 1 | | | | | Enzyme 2 | | | |
|---|---|---|---|---|---|---|---|---|---|---|
| Treatment | Type | Conc. (U/g) | T (° C.) | pH | t (h) | Type | Conc. (U/g) | T (° C.) | pH | t (h) |
| A | YL-NL | 21 | 50 | 6.5 | 1 | Prot N | 700 | 50 | 7.5 | 1 |
| B | Prot N | 5000 | 50 | 7.5 | 1 | — | — | — | — | — |
| C | YL-NL | 21 | 50 | 6.5 | 1 | Alcalase | 0.11 | 60 | 7 | 1 |
| D | YL-NL | 21 | 50 | 6.5 | 1 | Prot N | 5000 | 50 | 7.5 | 1 |

Example 3

Figure 4:
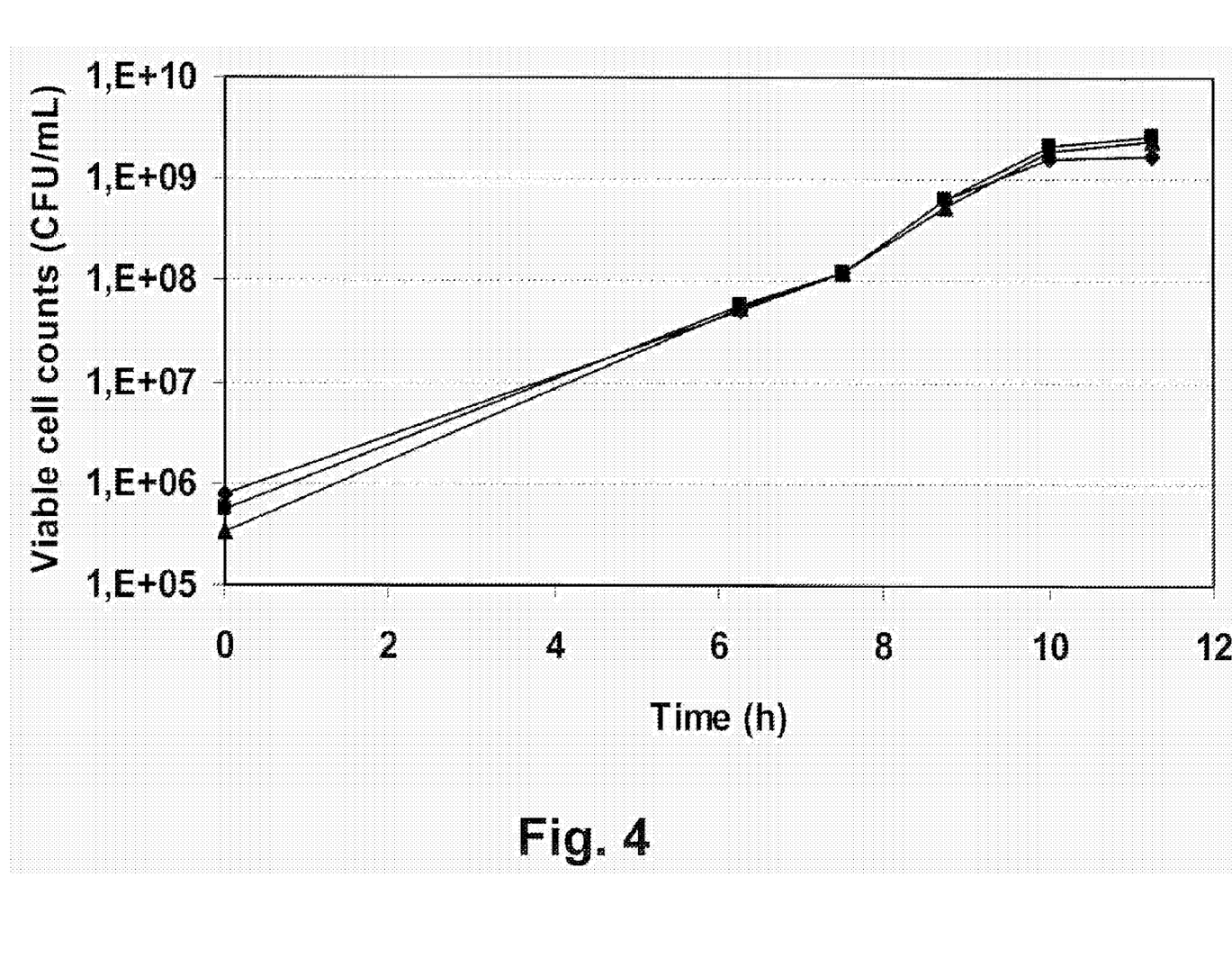
FIG. 4: Growth curve of La-5 in a yeast digest based medium

Small-Scale Production of Freeze-Dried Pellets of La-5 in a Digested Yeast Based Medium A fermentation was carried-out in triplicate using Provesta 027 digested with Alcalase from Novozymes (0.11 U/g) and a 5'-ribonuclease with the additional yeast extracts Biospringer 232 and Flavormate 957 (0.55% each). FIG. 4 shows the growth curves for La-5. The average final viable cell count reaches a high value of $2.25 \cdot 10^9 \pm 5.16 \cdot 10^8$ CFU/ml.

After fermentation the fermentate was concentrated by centrifugation 14-times, a commercially used cryoprotectant was added to the concentrate at an inclusion rate of 14.5% and the pellet was resuspended by agitation. The final suspension was then dropped into liquid nitrogen, the frozen pellets were harvested and kept at −70° C., and subsequently freeze-dried. Viable cell counts for the pre-freeze-dried (PFD) and freeze-dried (FD) pellets were $6 \cdot 10^9$ and $8.5 \cdot 10^{10}$ CFU/ml, respectively.

Example 4

Growth of *L. plantarum* Lp-346 on a Yeast Digest Based Medium

Materials & Methods

Microorganisms and Inoculum Preparation

The strain *Lactobacillus plantarum* Lp-346 (DSM4787, ATCC55943) was obtained from the Chr Hansen Culture Collection (CHCC 4230). The inoculum was prepared in modified BS 232 medium (5% BS232; 3% sugar). Two 10-hour serial transfers, maintained without control of the atmosphere at 37° C. using a transfer volume of 0.7% (v/v) were conducted. The fermenters were inoculated with 0.7% (v/v) of the final culture.

Culture Media

An 10% (w/w) aqueous suspension of the yeast source (Aventine 62-P or Provesta 027) was prepared. The suspension was heated to 90° C. for 20 min. After that period, the temperature and pH value were adjusted and controlled, the specific enzyme(s) were added and the digestion was carried-out. Optionally, the digestion was completed by the addition of a second enzyme followed by a second digestion period. The resulting suspension is referred to as "yeast digest". The medium was prepared by adding several other components (e.g. water, carbohydrates, mineral salts, and commercial yeast extracts if needed) to make it a complete medium for optimal growth of the micro-organisms. A partial composition of the medium is indicated in table 7. The medium was sterilized at 121° C. for 20 min and then cooled down rapidly on ice.

TABLE 7

Composition of the yeast digest based medium.

| Component | Amount (% w/w) |
|---|---|
| Yeast source | 1.75 |
| Proteolytic enzyme (e.g. Alcalase) | 0.08 |
| Yeast extract Biospringer 232 | 0.25, 0.55, 1 |
| Yeast extract Flavormate 957 | 0.25, 0.55, 1 |
| Sugar (e.g. dextrose monohydrate) | 4 |

Fermentations

Fermentations were carried-out in yeast digest based medium and meat based production medium at 37° C. and pH regulated at a value of 5.5 by addition of 13.5N $NH_4OH$. The cultures were performed in 2 L bioreactors (Xplora; Adaptive Biosystems, UK) with working volumes of 1.7 L. Initial pH of the culture medium was adjusted to 6.4 if necessary and the headspace was flushed with nitrogen before inoculation. Samples were taken at different time intervals, depending on base addition rate for analysis of residual sugar, L-lactic acid, and viable biomass concentration.

Cell Enumeration

Viable cell counts (CFU per milliliter) were determined by plating diluted samples on solid MRS agar. Plates were incubated without control of the atmosphere at 37° C. for two days.

Results

Effect of the Medium on the Growth of Lp-346

Several cultures were carried-out to investigate the effect of the medium on the growth of Lp-346. Table 8 shows the different media used. Medium A is an industrial medium based on the yeast extract Biospringer 232 at a concentration of 5%. Medium B is an industrial medium based on beef stock (1.4%) and the yeast extract Amberex 695 (2%). Media C to F are based on yeast digest, medium C using as a yeast source the whole yeast Aventine 62-P and media D, E, and F the autolyzed yeast Provesta 027. In media C, D, and E a mixture of the two yeast extracts Biospringer 232 and Amberferm 1857 are used at an inclusion rate of 0.25% each. Medium F contains the yeast extract Amberex 695 at an inclusion rate of 1%.

Sterilization of the media were carried-out in two different ways. Either all the medium were mixed together and subsequently heat treated (T) at 121° C. for 20 min., or the protein containing ingredients were heat treated and the sugars were dissolved in a second portion of water, sterile filtered (F) and the two portions were mixed.

Figure 5:
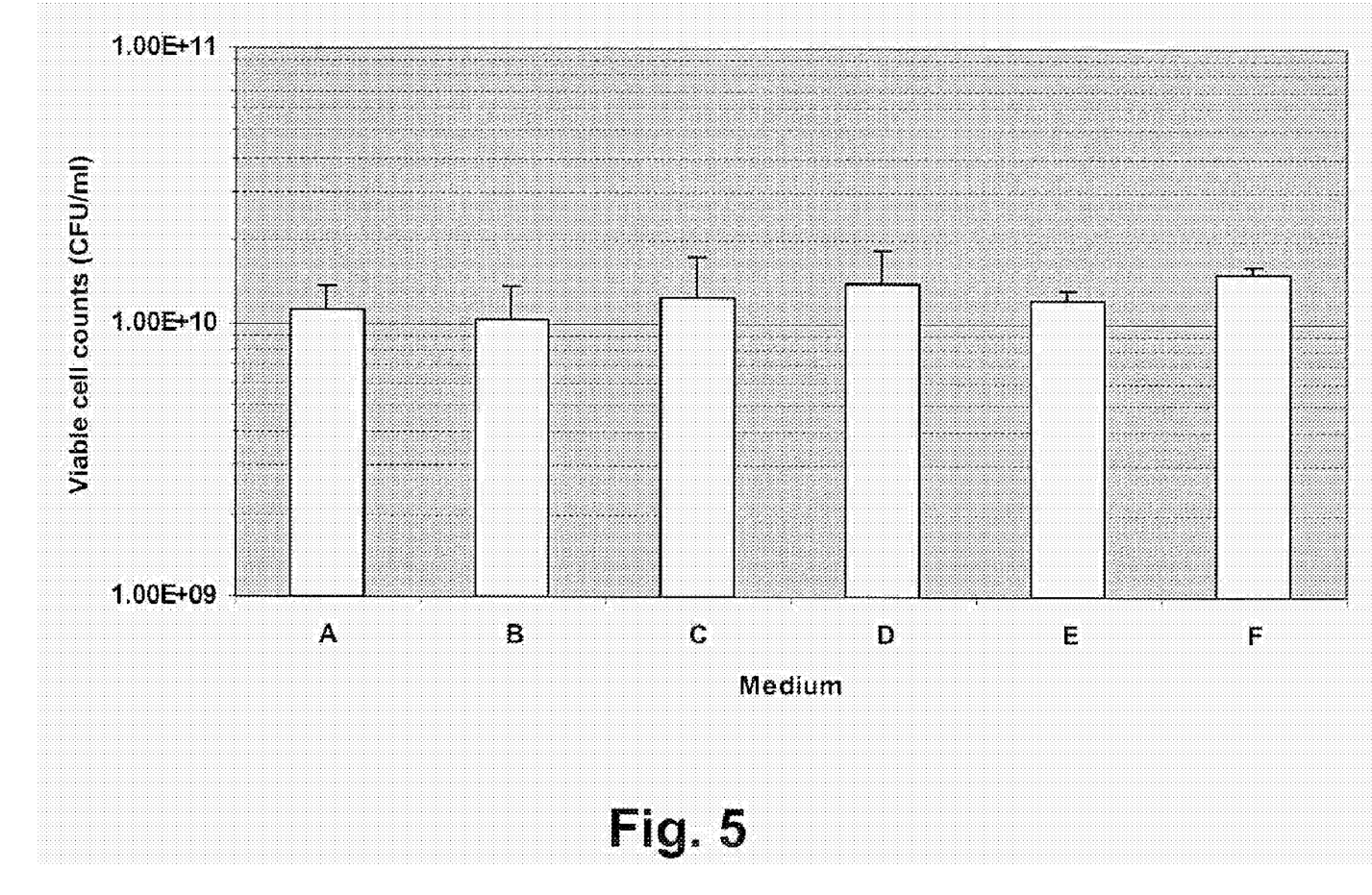
FIG. 5: Final viable cell counts of *L. plantarum* Lp-346 grown in different media.

Table 9 and FIG. 5 show the final cell counts obtained for each medium. Despite the considerable reduction in protein containing raw material from 5% (Medium A), 3.4% (Medium B) to 2.25% (Medium C, D, E) and 2.75% (Medium F), there is no significant difference (p<0.05) in final cell counts for all media tested. Therefore, the yeast digest based medium can actually be used to replace the currently used growth medium for the tested strain.

TABLE 9

Media for the growth of Lp-346

| Medium | Type | Yeast | YE | Sterilization Method | Final VPC (CFU/ml) |
|---|---|---|---|---|---|
| A | BS 232 | — | BS 232 | T | $1.11 \cdot 10^{10}$ |
| B | Meat extract | — | Amberex 695 | T | $1.03 \cdot 10^{10}$ |
| C | Digest | Aventine | Mix | T | $1.23 \cdot 10^{10}$ |
| D | Digest | Provesta | Mix | T | $1.41 \cdot 10^{10}$ |
| E | Digest | Provesta | Mix | F | $1.20 \cdot 10^{10}$ |
| F | Digest | Provesta | Amberex 695 | F | $1.51 \cdot 10^{10}$ |

Example 5

Small Scale Production of Freeze-Dried Pellets of Lp-346 in a Digested Yeast Based Medium Medium was prepared as described before using Provesta 027 as a yeast source and the yeast extract Amberex 695 at an inclusion rate of 1%. The protein containing components of the medium were sterilized by heat treatment and then mixed with a sterile filtered dextrose solution.

Figure 6:
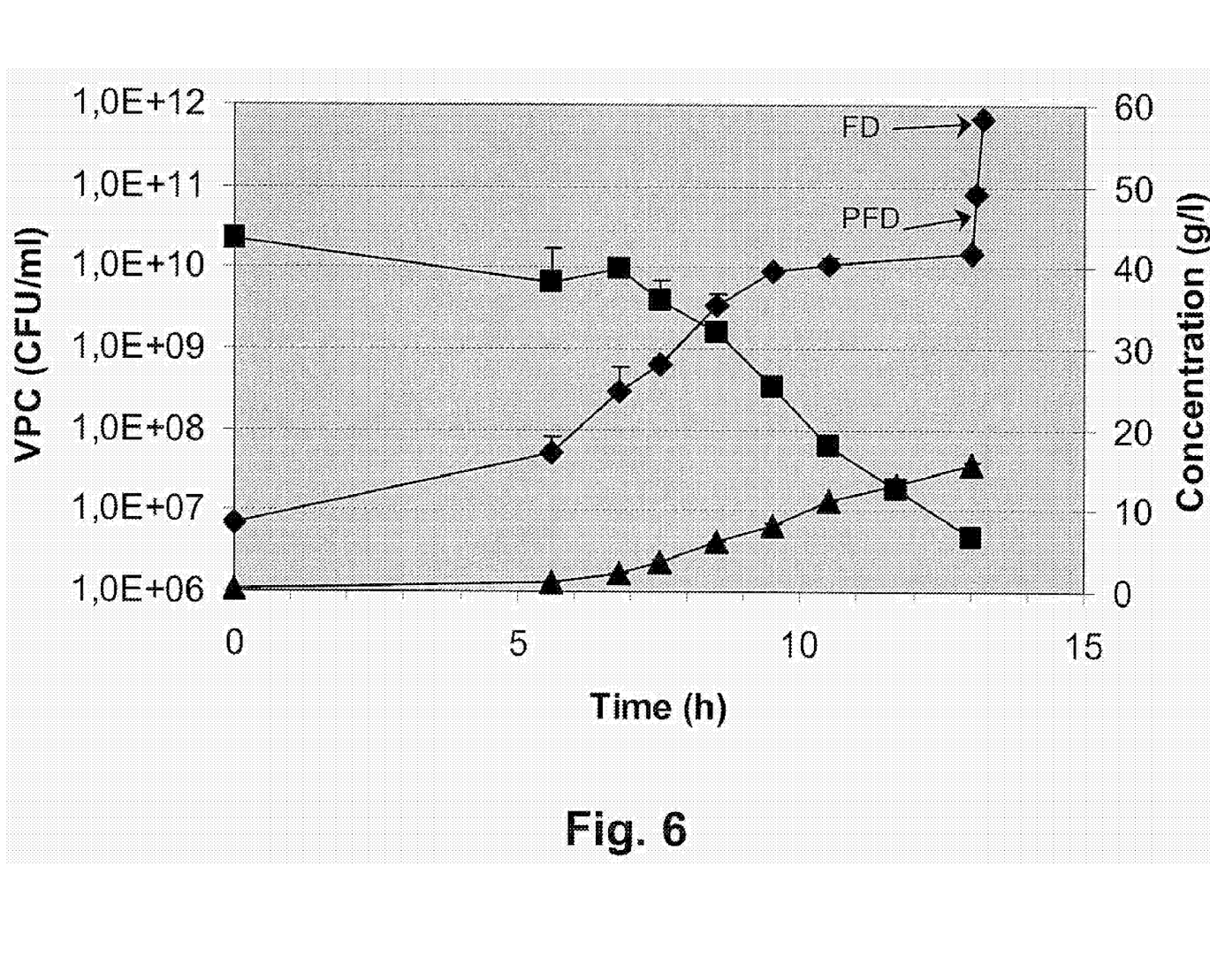
FIG. 6: Average cell counts (♦) of three fermentation of a yeast digest based medium with Lp-346 and of pre-freeze-dried (PFD) pellets and freeze-dried (FD) pellets. Concentrations of dextrose (■) and L-lactate (▲) during fermentation.

FIG. 6 shows the average growth curve of La-5 during three cultures with a final viable biomass of $1.53 \cdot 10^{10} \pm 1.32 \cdot 10^{9}$ CFU/ml.

After fermentation the fermentate was concentrated by centrifugation 14-times, a commercially used cryoprotectant was added to the concentrate at an inclusion rate of 17.5% and the pellet was resuspended by agitation. The final suspension was then dropped into liquid nitrogen, the frozen pellets were harvested and kept at −70° C., and subsequently freeze-dried.

Viable cell counts for the pre-freeze-dried (PFD) and freeze-dried (FD) pellets were $8.25\pm1.38\cdot10^{10}$ and $6.73\pm0.83\cdot10^{11}$ CFU/ml, respectively.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

U.S. Pat. No. 6,159,724 A
GB 1516333 A
U.S. Pat. No. 6,294,166 B1

All references cited in this patent document are hereby incorporated herein in their entirety by reference.

The invention claimed is:

1. A method for preparing a composition comprising a culture of viable microorganisms, said method comprising:
   a) treating an aqueous suspension of whole yeast cells and/or a lysate thereof, with one or more enzymes selected from the group consisting of an enzyme capable of digesting cell components, an enzyme capable of digesting the yeast cell wall, a proteinase, a lipase, a glucanase, an amylase, a nuclease, and a lyase to digest the whole yeast cells or a lysate thereof; and
   b) optionally inactivating the activity of the enzyme(s);
   c) optionally repeating step a) or steps a) and b);
   d) inoculating said treated suspension with a microorganism; and
   e) isolating/harvesting the obtained viable microorganisms,
wherein the suspension of step a) is free of wheat germs or whole meal.

2. The method of claim 1, wherein the aqueous suspension of step a) is obtained by the method comprising:
   i) heating the suspension to a temperature in the range 40-100 degrees C., and optionally maintaining the temperature for a period of 2-30 min; and/or
   ii) treating the yeast cells with a cell wall digesting enzyme; and/or
   iii) erupting the yeast cells by chemical or mechanical means.

3. The method of claim 1, wherein the enzyme(s) in step a) is heterologous to the yeast cells to be treated.

4. The method of claim 1, wherein the enzyme in step a) is selected from one or more of the group consisting of:
   a. a protease selected from the group consisting of: an enzyme belonging to the class EC 3.4.-.-, Protease N (Amano), subtilisin, and Alcalase (Novozymes);
   b. a lysing enzyme selected from the group consisting of: an enzyme belonging to the class EC 3.4.24.-, bacillolysin, and YL-NL (Amano);
   c. a nuclease selected from the group consisting of: an enzyme belonging to the class EC 3.1.3.- or 3.1.4.-, a Rnase, a DNase, and an exonuclease;
   d. an amylase selected from the group consisting of: an enzyme belonging to class EC 3.2.1.-, alpha amylase, and amyloglucosidase; and
   e. a lipase selected from the group consisting of: an enzyme belonging to class EC 3.1.1.-.

5. The method of claim 1, wherein the microorganism is a lactic acid bacteria.

6. The method of claim 1, further comprising one or more of the following steps:
   (i) aerating the mixture obtained in step d);
   (ii) agitating the mixture obtained in step d);
   (iii) drying the isolated microorganisms;
   (iv) drying the isolated microorganisms;
   (v) pelletizing the isolated microorganisms; or,
   (vi) packaging the isolated microorganisms.

7. The method of claim 1, wherein the lysate is an autolysate.

8. The method of claim 2, wherein step ii), if carried out, is carried out at a pH in the range 5-8 and/or at a temperature in the range 20-80 degrees C. and/or for a period of 10 minutes to 24 hours.

9. The method of claim 3, wherein the enzyme(s) in step a) is from a yeast species different from that of said yeast cells, is of non-yeast origin, is of bacterial origin, or is of fungal origin.

10. The method of claim 9, wherein the enzyme(s) in step a) is from a *Bacillus* species.

11. The method of claim 10, wherein the *Bacillus* species is *B. subtilis*.

12. The method of claim 9, wherein the enzyme(s) in step a) is from an *Aspergillus* species.

13. The method of claim 4, wherein the protease is an enzyme of class EC 3.4.21.62.

14. The method of claim 4, wherein the nuclease is an enzyme of class EC 3.1.4.1.

15. The method of claim 5, wherein the lactic acid bacteria are of a species from a group selected from *Lactobacillus*, *Lactococcus*, and *Leuconostoc*.

16. The method of claim 15, wherein the lactic acid bacteria are of a *Lactobacillus* species selected from the group consisting of *L. acidophilus, L. casei, L. bulgaricus*, and *L. helveticus*.

17. The method of claim 15, wherein the lactic acid bacteria are of a *Lactococcus* species selected from the group consisting of *L. lactis, L cremoris, L. diacetylactis*, and *L. thermophilus*.

18. The method of claim 15, wherein the lactic acid bacteria are of the species *Leuconostoc cremoris*.

19. The method of claim 5, further comprising adding one or more nutrient component(s) before step e) selected from the group consisting of: a carbohydrate, a yeast extract, a beef extract, a peptone, a vitamin, a peptide, a protein, a mineral salt, a growth factor and a lipid.

20. The method of claim 19, wherein the one or more nutrient component is a peptone and the peptone is selected from the group consisting of a soy peptone, a wheat peptone, and a whey peptone.

21. The method of claim 5, wherein step d) is performed before step c).

22. The method of claim 6, wherein the isolated microorganisms are pelletized in freeze-dried form.

\* \* \* \* \*

UNITED STATES PATENT AND TRADEMARK OFFICE
CERTIFICATE OF CORRECTION

PATENT NO. : 8,361,778 B2 Page 1 of 1
APPLICATION NO. : 12/090112
DATED : January 29, 2013
INVENTOR(S) : Dirk Bergmaier It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1211 days.

Signed and Sealed this
First Day of September, 2015

Michelle K. Lee
*Director of the United States Patent and Trademark Office*